United States Patent [19]
Taylor et al.

[11] Patent Number: 5,456,680
[45] Date of Patent: Oct. 10, 1995

[54] FIBER OPTIC CATHETER WITH SHORTENED GUIDE WIRE LUMEN

[75] Inventors: Kevin D. Taylor; Jerome Bellendir; Dan J. Hammersmark, all of Colorado Springs, Colo.

[73] Assignee: Spectranetics Corp, Colorado Springs, Colo.

[21] Appl. No.: 120,385

[22] Filed: Sep. 14, 1993

[51] Int. Cl.$^6$ .................................................. A61B 17/36
[52] U.S. Cl. ................................ 606/2; 606/15; 606/7
[58] Field of Search ............................ 606/7, 15, 16, 606/10, 2, 11

[56] References Cited

U.S. PATENT DOCUMENTS

| | | |
|---|---|---|
| Re. 33,166 | 2/1990 | Samson . |
| 4,323,071 | 4/1982 | Simpson et al. . |
| 4,468,224 | 8/1984 | Enzmann et al. . |
| 4,573,470 | 3/1986 | Samson et al. . |
| 4,582,181 | 4/1986 | Samson . |
| 4,619,263 | 10/1986 | Frisbie et al. . |
| 4,641,654 | 2/1987 | Samson et al. . |
| 4,662,368 | 5/1987 | Hussein et al. . |
| 4,664,112 | 5/1987 | Kensey et al. . |
| 4,664,113 | 5/1987 | Frisbie et al. . |
| 4,748,982 | 6/1988 | Horzewski et al. ............... 128/344 |
| 4,757,827 | 7/1988 | Buchbinder et al. . |
| 4,762,129 | 8/1988 | Bonzel . |
| 4,775,371 | 10/1988 | Mueller . |
| 4,795,458 | 1/1989 | Regan . |
| 4,798,586 | 1/1989 | Stevens . |
| 4,808,164 | 2/1989 | Hess . |
| 4,832,024 | 5/1989 | Boussignac et al. . |
| 4,838,268 | 6/1989 | Keith et al. . |
| 4,841,976 | 6/1989 | Packard et al. . |
| 4,844,062 | 7/1989 | Wells . |
| 4,846,174 | 7/1989 | Willard et al. . |
| 4,846,193 | 7/1989 | Tremulis et al. . |
| 4,867,173 | 9/1989 | Leoni . |
| 4,869,246 | 9/1989 | Adair .............................. 606/7 |
| 4,874,371 | 10/1989 | Comben et al. . |
| 4,878,492 | 11/1989 | Smofsky et al. ...................... 606/7 |
| 4,898,577 | 2/1990 | Badger et al. . |
| 4,913,142 | 4/1990 | Kittrell et al. ........................ 606/15 |
| 4,917,102 | 4/1990 | Miller et al. . |
| 4,917,666 | 4/1990 | Solar et al. . |
| 4,923,462 | 5/1990 | Stevens . |
| 4,932,413 | 6/1990 | Shockey et al. . |
| 4,940,062 | 7/1990 | Hampton et al. . |
| 4,947,864 | 8/1990 | Shockey et al. . |
| 4,958,642 | 9/1990 | Christian et al. . |
| 4,998,917 | 3/1991 | Gaiser et al. . |
| 4,998,923 | 3/1991 | Samson et al. . |

(List continued on next page.)

FOREIGN PATENT DOCUMENTS 591963  7/1925  France .

OTHER PUBLICATIONS

Nordenstrom, "New Instruments for Catheterization and Angiocardiography", Radiology, Jul.–Dec. 1965, pp. 66–70.
Bonzel et al., "A New Catheter System for Coronary Angioplasty (PTCA) with Exchangeable Intracoronary Catheters High Flow of Contrast Agent, and Improved Steerability", Biomedizinische Technik, 1986, pp. 195–200.
Nordenstrom, "Balloon Catheters for Percutaneous Insertion Into the Vascular System", Mar. 2, 1962, pp. 411–416.

*Primary Examiner*—Stephen C. Pellegrino
*Assistant Examiner*—Sonya C. Harris
*Attorney, Agent, or Firm*—Cushman, Darby & Cushman

[57] ABSTRACT

A fiber optic catheter has a short guide wire lumen (less than 10 cm) extending in a proximal direction from its distal end and an intermediate portion reinforced with a tapered mandrel which provides optimal steerability and trackability characteristics. The distal end of the mandrel is coextensive with a proximal portion of the guide wire lumen. The intermediate portion of the catheter may have a marker for visual identification, and the tip of the catheter may include a radiopaque tip marker band for fluoroscopic identification. The short guide wire lumen catheter provides superior flexibility, a low profile, and low-friction engagement with the guide wire.

33 Claims, 6 Drawing Sheets

U.S. PATENT DOCUMENTS

| | | |
|---|---|---|
| 5,002,553 | 3/1991 | Shiber . |
| 5,007,896 | 4/1991 | Shiber . |
| 5,009,655 | 4/1991 | Daignault et al. . |
| 5,009,659 | 4/1991 | Hamlin et al. . |
| 5,024,234 | 6/1991 | Leary et al. . |
| 5,026,366 | 6/1991 | Leckrone ................................. 606/7 |
| 5,026,384 | 6/1991 | Farr et al. . |
| 5,035,686 | 7/1991 | Crittenden et al. . |
| 5,040,548 | 8/1991 | Yock . |
| 5,045,061 | 9/1991 | Seifert et al. . |
| 5,055,109 | 10/1991 | Gould et al. . |
| 5,059,176 | 10/1991 | Winters . |
| 5,061,273 | 10/1991 | Yock . |
| 5,114,403 | 5/1992 | Clarke et al. . |

Fig. 13

FIBER OPTIC CATHETER WITH SHORTENED GUIDE WIRE LUMEN

BACKGROUND OF THE INVENTION

1. Field of the Invention

The present invention relates to catheters used for surgical operations, and more specifically, to fiber optic catheters used for illuminating and ablating intravascular regions and means for guiding and positioning such catheters.

2. Description of the Related Art

Percutaneous transluminal coronary angioplasty (PTCA) is a technique for opening arterial constrictions and partial blockages called stenoses that arise from deposition of cholesterol and fibrous tissue in the walls of coronary arteries.

The human heart has three main coronary arteries which supply oxygenated blood to the heart. The opening in the aorta which marks the origin of the coronary arteries is called the ostium. In PTCA, the operator makes a puncture in an artery (usually a femoral artery in the groin) and passes a catheter up the artery past the ostium and into the coronary artery. The catheter may be a balloon catheter having at its end a balloon which, when inflated at the position of the stenosis, causes compression, stretching and splitting of the stenotic material and often expansion of the arterial wall, thereby enlarging the blood flow channel. Alternatively, the catheter may be a fiber optic catheter which uses optical fibers disposed within the catheter body to deliver energy from a source of high-intensity light (e.g., a laser) to the stenosis to ablate it. The catheter may also be of the cautery type, which uses a heated element to burn the stenosis away.

PTCA is an established technique and is used as an alternative to a bypass operation in which a section of vein, usually from the patient's leg, is used to bypass the stenosis. PTCA is performed by cardiologists and radiologists whereas by-pass surgery is carried out by cardiac surgeons. The patient in PTCA only has a local anesthetic for insertion of an introducer sheath into the femoral artery. Thereafter, a guide catheter is fed through the sheath to the ostium. The guide catheter is followed by the catheter. After successful dilatation, the patient is kept in the hospital for only one or two days and can return to work within about a week. Thus, the benefit of PTCA can be seen by contrasting it with bypass surgery which requires major surgery under full anesthesia, one or two weeks in hospital, and a substantial period of convalescence.

One type of PTCA catheter is the over-the-wire (OTW) catheter. An OTW balloon catheter has two lumens, one for inflation of the balloon at its distal end and the other for passage of a guide wire. An OTW fiber optic catheter has a coaxial lumen including an innermost lumen for the passage of a guide wire surrounded by optical fibers encapsulated by the outer lumen.

When an OTW catheter is used in PTCA, a puncture is made (again, usually in the femoral artery) and a guide catheter about 100 centimeters long is inserted into the puncture and passed into the ostium. The OTW catheter (about 135 centimeters long) is threaded over the guide wire (about 175 centimeters long) and the catheter and the guide wire are passed up the guide catheter to the ostium. Then, the guide wire is carefully slid down the coronary artery past the stenosis. The OTW catheter is slid out of the guide catheter and down the guide wire until its distal end is at the site of the stenosis. Then, in the case of a balloon OTW catheter, the balloon is inflated to dilate the artery as described above. In the case of a fiber optic catheter, the distal end of the catheter delivers light energy to the stenosis to ablate and remove it.

OTW catheters are a considerable advance over fixed wire catheters, since the guide wire can be positioned and manipulated independently to ensure that the correct artery is selected. OTW catheters also enable a doctor to monitor the position of the catheter more easily than can be done with a fixed tip design. To ensure that a fixed tip catheter is properly positioned, the doctor has to inject X-ray contrast fluid at frequent intervals. This is not obviated by the over-the-wire catheters per se, but the use of a guide wire does enable the doctor to see the wire on an X-ray fluoroscopy screen, thereby allowing him or her to control the position of the catheter.

During a PTCA procedure, it is often necessary to change OTW catheters. With conventional OTW designs, the doctor cannot withdraw the catheter while leaving the guide wire in place without significant effort. Thus, the doctor must first attach an extension to the guide wire so that the total length is about 300 centimeters. As a less preferred alternative, the guide wire can be withdrawn and substituted with one about 300 centimeters long. Thereafter, the catheter is slid off the guide wire and another catheter is substituted.

This procedure for changing catheters is cumbersome because it requires two operators to hold the guide wire, remove the first catheter and feed the replacement onto the wire. If the guide wire is removed and replaced, the patient is exposed to risk because the doctor must pass a guide wire across the stenosis for second time. It also exposes the patient to an unwanted amount of radiation, since the time required to accomplish the procedure is extended.

Some catheters have been developed which have guide wire lumens that are substantially shorter than the overall catheter body length. U.S. Pat. Nos. 5,040,548 and 5,061,273 to Yock, for example, disclose a balloon catheter having a guide wire lumen at least 10–15 centimeters long extending from the catheter's distal tip toward its proximal end. U.S. Pat. No. 4,762,129 to Bonzel discloses a similar balloon catheter where the shortened guide wire lumen is formed in the interior of and is substantially coextensive with the balloon interior. Similarly, U.S. Pat. No. 4,662,368 to Hussein et al. discloses a catheter for removing stenoses by cauterizing them with a heated tip in which the tip has a short channel for accommodating a guide wire.

U.S. Pat. No. 4,468,224 to Enzmann et al. discloses a non-PTCA catheter which, in one embodiment, uses a guide wire threading aperture set at a large angle and disposed at a moderate distance behind the catheter's distal end to introduce a guide wire into the catheter's central lumen.

It is important to note that though the above prior art catheters make use of a shortened guide wire lumen, the lumen must still be of a significant length (e.g., in the Yock device, at least 10 cm). If the guide wire lumen length is too short, the Yock patents teach that the wire cannot reliably guide the catheter to the stenosis. Instead, the flexible catheter will tend to bend and kink, thereby impeding proper positioning.

SUMMARY OF THE INVENTION

While the above designs alleviate the problems associated with catheter exchanges to some degree, they are not without their disadvantages. For example, the interior surface area of the long guide wire lumen gives rise to undesirable frictional forces between the lumen interior and the guide wire.

Further, the ability of the catheter to track tortuous passageways is decreased by the additional stiffness imparted to the catheter's distal end by the long guide wire portion and lumen lying therein. Also, the longer guidewire lumen catheters are more cumbersome to exchange than shorter guidewire lumen catheters.

It is therefore an object of this invention to provide a fiber optic catheter exhibiting superior tracking qualities which can easily be exchanged on a stationary standard length (about 175 cm) guide wire.

It is a further object of this invention to provide a fiber optic catheter having a shortened, low-friction guide wire lumen.

It is still a further object of this invention to provide a fiber optic catheter having a shortened guide wire lumen which has a reduced tendency to kink, bend and exhibit guide wire prolapse.

It is yet another object of this invention to provide a fiber optic catheter having a low midsection profile, thereby minimizing trauma to body vessels through which it passes and improving the quality of contrast injection-enhanced fluoroscopic visualization.

The above objects are achieved by providing a fiber optic catheter having a shortened guide wire lumen (less than 10 cm) extending in a proximal direction from its distal end. An intermediate portion may contain a mandrel having a varying stiffness profile, where the distal end of the mandrel is coextensive with a proximal portion of the guide wire lumen. Preferably, the optical fibers are fixed no more than once within the distal 20 cm of the catheter, thereby allowing the catheter to flex with minimal force. For example, the optical fibers may be fixed at a distal end of the catheter by a glue plug. The optical fibers are not otherwise obstructed in the distal 20 cm of the catheter, thereby maintaining flexibility.

BRIEF DESCRIPTION OF THE DRAWINGS

These and other objects and advantages of this invention will become apparent and more readily appreciated from the following description of the presently preferred exemplary embodiments, taken in conjunction with the accompanying drawings, of which.

DETAILED DESCRIPTION OF THE PRESENTLY PREFERRED EXEMPLARY EMBODIMENTS

Figure 1:
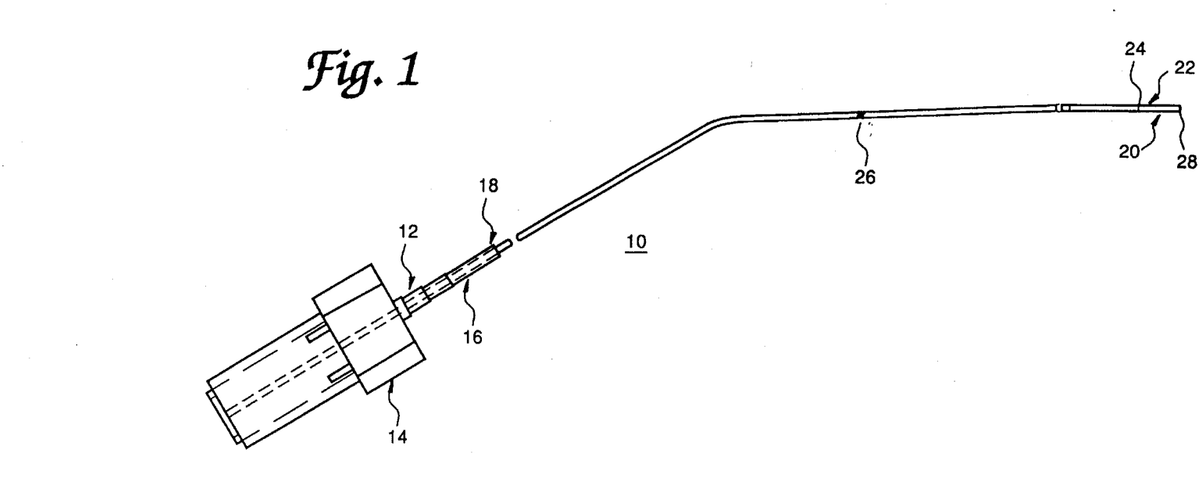
FIG. 1 is a perspective view of a fiber optic catheter according to the present invention.

FIG. 1 depicts a perspective view of a fiber optic catheter 10 according to the present invention. A proximal end 12 of a tail tube 16 is connected to a proximal mount 14. The proximal mount 14 may be a two-piece mount as described in U.S. patent application Ser. No. 07/899,470 to Nielson et al., incorporated herein by reference, and it may be of the linear scan type described in U.S. patent application Ser. No. 07/882,597 to Grace et al., also incorporated herein by reference. The tail tube 16 has an optical fiber bundle (not shown) disposed therein, and the proximal ends of fibers in the bundle are affixed to the proximal mount 14 using techniques known in the art or disclosed in the above-referenced applications.

The distal end of the tail tube 16 is attached to an outer jacket 18 which further accommodates the optical fiber bundle. The tail tube 16 and the outer jacket 18 collectively form a catheter body. The outer jacket 18 may have a proximal marking 26 on it for visual identification of the degree of insertion of the catheter 10. The distal end of the outer jacket 18 includes a guide portion 20 having a shortened guide wire lumen body 22 passing therethrough for accommodating a guide wire 24. The distal end of the guide portion 20 may be terminated by a radiopaque tip marker band 28 for fluoroscopic visualization of the catheter 10 in situ. Also, the guide wire 24 may be of conventional design or, more advantageously, may be of a type capable of delivering light energy itself. Such a fiber optic guide wire is described in more detail in U.S. patent application Ser. No. 07/930,934 to Kasparzyk et al., incorporated herein by reference.

The tail tubing 16 and the outer jacket 18 may be constructed from any of a number of suitable materials, such as plasticized vinyl resins, polyethylene, synthetic and natural rubbers and polyurethane elastomers. Preferably, the tail tube 16 is about seventy-two inches long and is constructed from a high durometer polyester elastomer material such as 0.062" OD Dupont Hytrel® 72D tubing. The outer jacket 18 is preferably a 129 cm length of Hytrel® 55D tubing with a low-friction hydrophilic coating such as that made by the BSI corporation on its distal 35 centimeters to enhance trackability. After the necking processes described below, the diameter of the jacket is about 0.045" outside diameter (OD). The radiopaque tip marker band 28 is preferably made from a platinum or a radiopaque alloy thereof. The guide portion 20 is advantageously a nine centimeter length of 0.060" OD Hytrel® 40D tubing, and the guide wire lumen body 22 disposed therein is most advantageously made from polyethylene or polyester elastomer tubing to provide a low-friction surface contacting guide wire 24. The use of gradually lower durometer materials towards the distal tip of catheter 10 increases the flexibility of the catheter tip, thereby enhancing the catheter's trackability.

Figure 8:
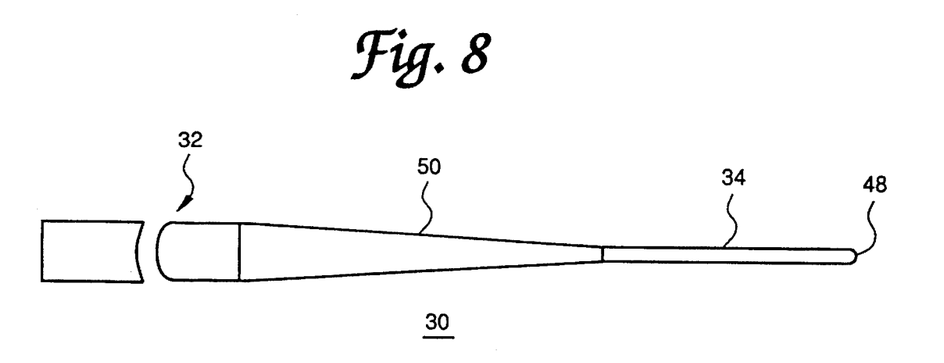
FIG. 8 is a longitudinal view of the mandrel used in the catheter of FIG. 1.

FIGS. 2–5 depict the tail tube 16, the outer jacket 18 with the proximal marker 26 thereon, and the guide portion 20 having the guide wire lumen body 22 disposed therein and the radiopaque tip marker band 28 at its distal end. The distal portion of the catheter 10 includes a mandrel 30 passing from the tail tube 16 through the outer jacket 18 to the guide portion 20. As shown more clearly in FIG. 8, the mandrel 30 may have a proximal portion 32 of substantially constant diameter (preferably about 0.0195" in diameter) and about 48.5" long. Tapered portion 50 is about 5.9" long, tapering to a diameter of 0.0095". Distal portion 34 is preferably about 3.5" long and has a constant diameter of 0.0095" and the distal taper 52 is about 0.25" long and tapers to about 0.005" diameter. Distal tip 48 is preferably about 0.005" in diameter and about 1.1" long. About two centimeters of the distal portion of the mandrel 30 overlaps with the proximal end of the guide wire lumen body 22 along the length of the catheter 10. By varying the dimensions of the mandrel 30, an optimal stiffness profile can be imparted to the catheter 10 to enhance its trackability and steerability characteristics. Of course, methods other than varying the thickness of the mandrel 30 may be used to vary its stiffness; for example, the mandrel 30 may be constructed from compositions of varying flexibility, or it may be equipped with variable-depth incisions along its length to increase its flexibility.

Figure 2:
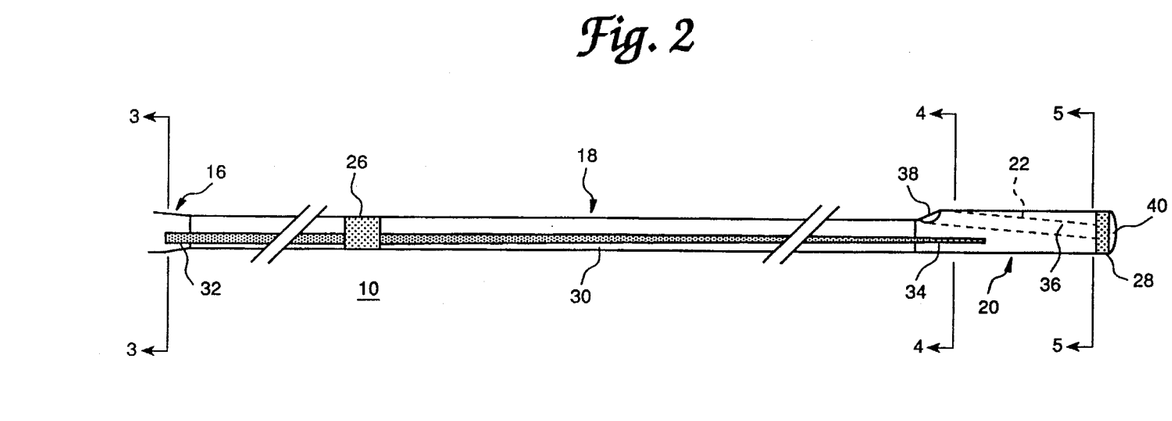
FIG. 2 is a schematic longitudinal cross-sectional view of a distal portion of the catheter of FIG. 1 with optical fibers removed for clarity.
Figure 6:
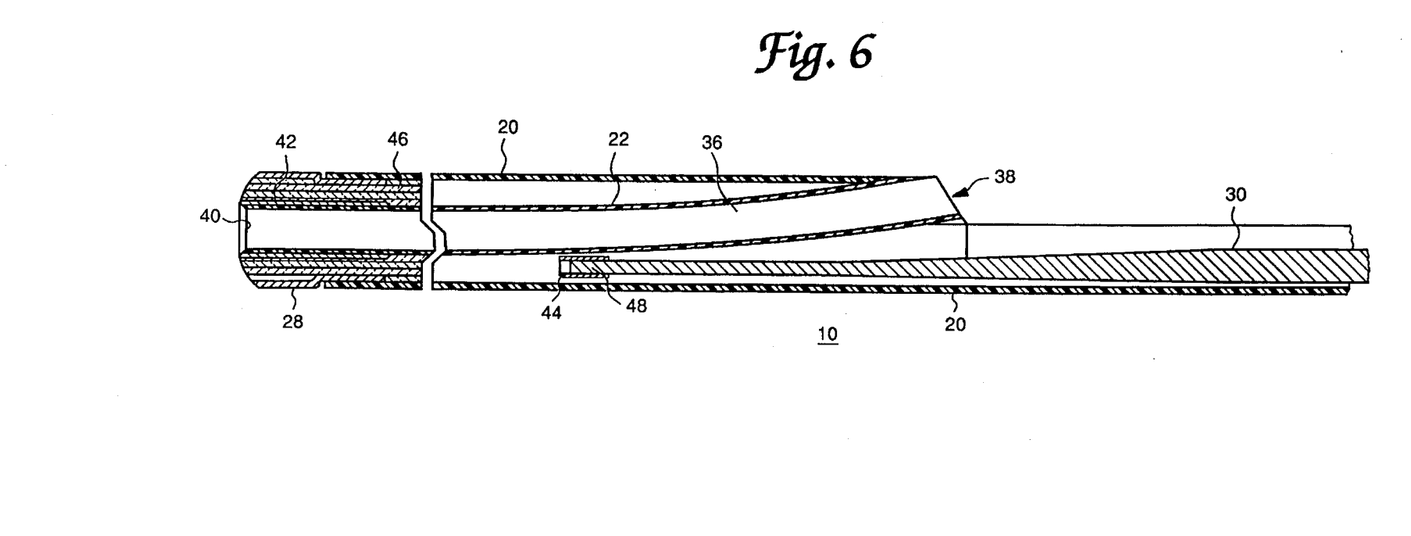
FIG. 6 is a detailed longitudinal cross-sectional view of the distal end of the catheter of FIG. 1 with optical fibers partially removed for clarity.

As shown in FIG. 6, the distal tip 48 of mandrel 30 is covered by protective jacket 44 which is a short (preferably about 7–8 mm) length of Hytrel® tubing which protects guide wire lumen body 22 from being inadvertently punctured by the tip of mandrel 30 when the catheter is flexed in the downward direction of FIGS. 2 and 6.

Also shown in FIGS. 2 and 6 is the guide wire lumen body 22 defining a guide wire lumen 36 having a guide wire entry port 38 at its proximal end at an angle of approximately 40°–60° to a plane perpendicular to the longitudinal axis of the catheter and a guide wire exit port 40 substantially concentric with the guide portion 20 at the distal end of the catheter 10. In contrast to the relatively long guide wire lumens in prior art designs, the guide wire lumen 36 in the present invention is less than ten centimeters in length, and is advantageously six to ten centimeters long. Preferably, guide wire lumen 36 is nine centimeters long.

Figure 3:
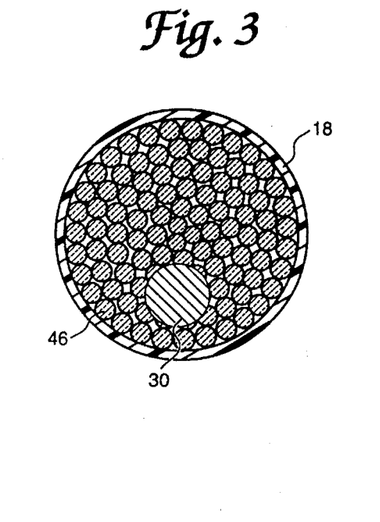
FIG. 3 is a transverse cross-sectional view of the distal end of the catheter of FIG. 1 taken along line 3—3 of FIG. 2.
Figure 4:
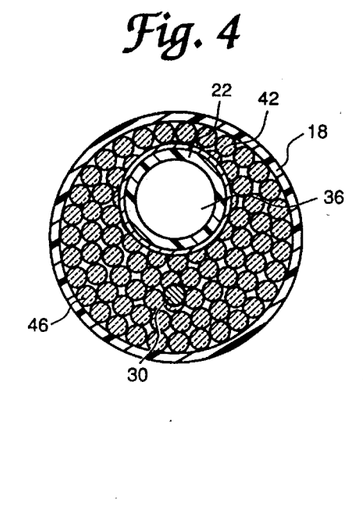
FIG. 4 is a transverse cross-sectional view of the distal end of the catheter of FIG. 1 taken along line 4—4 of FIG. 2.
Figure 5:
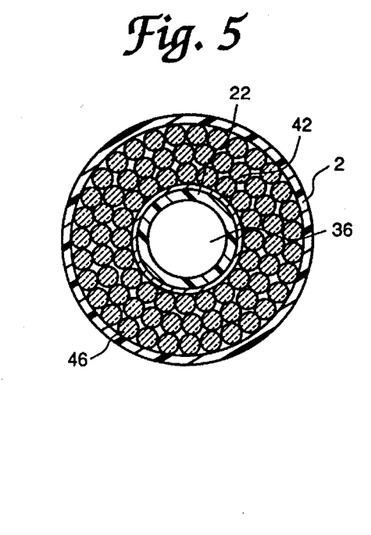
FIG. 5 is a transverse cross-sectional view of the distal end of the catheter of FIG. 1 taken along line 5—5 of FIG. 2.

For simplicity and clarity, the optical fiber bundle 46 has not been shown in FIG. 2 or in the proximal portion of FIG. 6; however, as seen in FIGS. 3–5, it is disposed in the interior portions of tail tube 16, the outer jacket 18 and the guide portion 20 that are not occupied by the mandrel 30 or the guide wire lumen body 22 and guide wire lumen 36. Preferably, the optical fibers comprising bundle 46 have a diameter of approximately 61 μm.

The tip of the catheter 10 may be terminated by radiopaque tip marker band 28 alone, or it may be complemented by an additional inner band proximate to the guide wire lumen body 22 in the manner of the two-piece optical fiber catheter tip described in U.S. patent application Ser. No. 07/857,458 to Grace et al., incorporated herein by reference.

Figure 7:
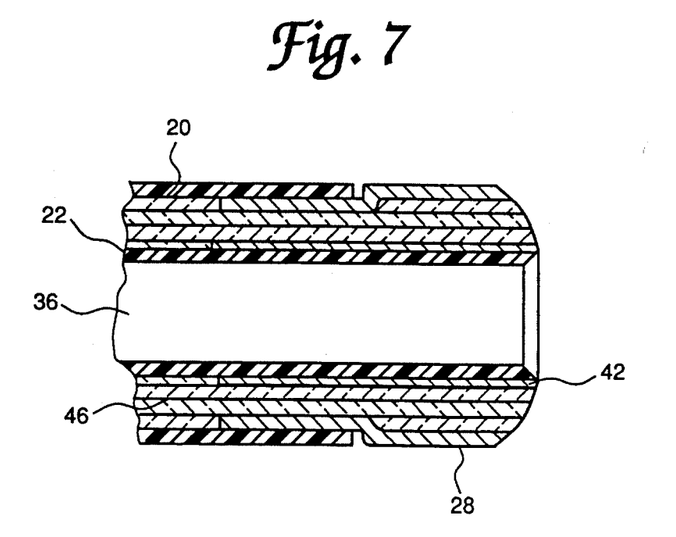
FIG. 7 is a more detailed longitudinal cross-sectional view of the tip of the catheter of FIG. 1.

Thus, as shown in FIG. 6 and more clearly in FIG. 7, the distal end of guide wire lumen body 22 is covered by inner band 42 (preferably a rigid 0.027 ID, 0.032 OD #304 stainless steel tube about 0.05–0.06" long) which provides structural integrity to the catheter tip to enhance trackability and to provide a durable end element able to withstand intense light energy reflections, pressure pulses, and other highly localized effects of the ablation process. Inner band 42 is disposed on the exterior of guide wire lumen body 22 to avoid a high friction metal-to-metal contact with guide wire 24.

Figure 9:
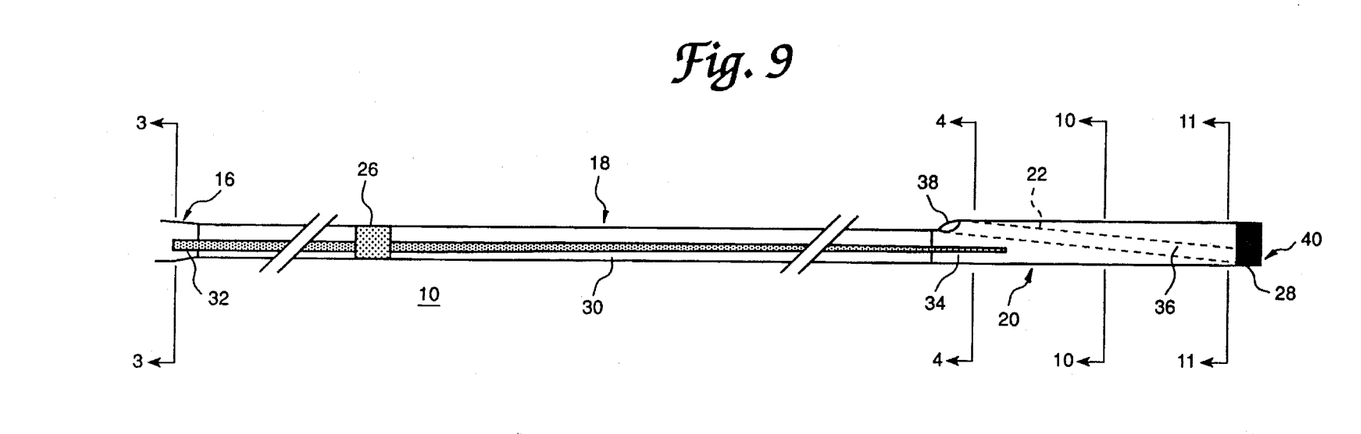
FIG. 9 is a detailed longitudinal cross-sectional view of another embodiment of a catheter according to the present invention with optical fibers removed for clarity.
Figure 10:
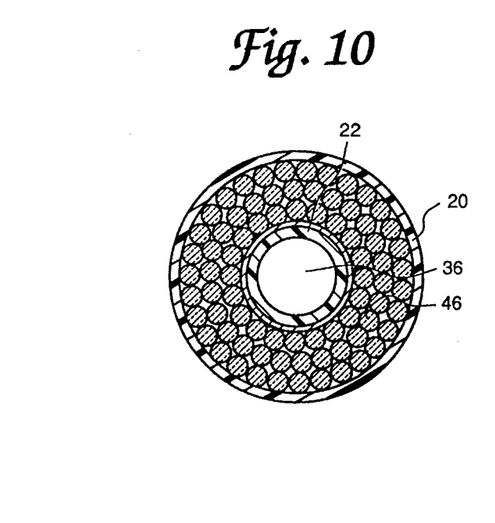
FIG. 10 is a transverse cross-sectional view of the distal end of the catheter of FIG. 9 taken along line 10—10 of FIG. 9.
Figure 11:
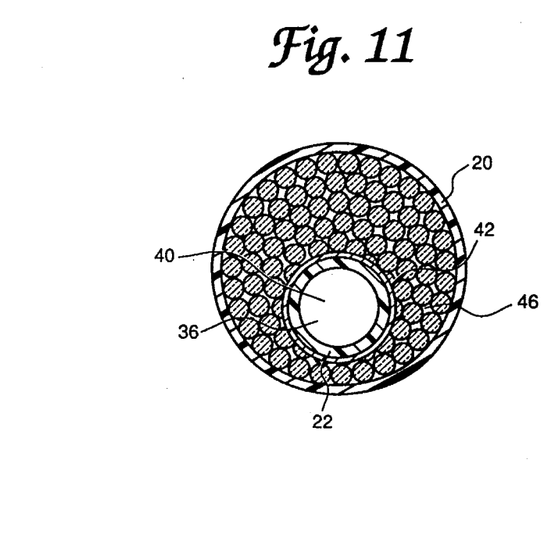
FIG. 11 is a transverse cross-sectional view of the distal end of the catheter of FIG. 9 taken along line 11—11 of FIG. 9.

While FIGS. 1–8 depict a fiber optic catheter having a distal guide wire lumen port concentric with the catheter body, other configurations may be utilized without departing from the spirit and scope of the invention. For example, FIGS. 9–11 show a shortened guide wire lumen catheter having a guide wire lumen body 22 extending from a guide wire entry port 38 as in the previous embodiment to an eccentric distal guide wire port 40 displaced from the longitudinal axis of catheter 10. As can clearly be seen in FIGS. 9 and 11, the guide wire exit port 40 is disposed on a side of the catheter axis opposite the guide wire entry port 38; however, in some cases it may be useful to incorporate an eccentric guide wire lumen body 22 running substantially horizontally and parallel to the catheter axis to an eccentric guide wire exit port on the same said of the axis as the entry port 38.

A method of making the present invention will now be described. First, the guide wire lumen body 22 is cut from a suitable piece of tubing and inner band 42 is placed over one end and bonded thereto with a suitable adhesive such as cyanoacrylate adhesive. Then, outer jacket 18 and guide portion 20 are cut from suitable pieces of tubing, and the ends are overlapped and fused together to form the catheter body. During the fusion process, a port 38 is left open at the joint to accommodate guide wire lumen body 22.

Next, the distal end of the guide wire lumen body 22 with inner band 42 attached thereto is placed in the middle of the distal end of the optical fiber bundle 46 and the fibers and body 22 are pulled through the radiopaque band 28 and the catheter body. After the fiber bundle 46 is in place, a suitable adhesive such as epoxy is wicked up the fibers from the catheter's distal tip and cured by a suitable process such as UV curing or heat treatment.

After curing the distal catheter tip, the portion of the optical fiber bundle 46 and guide wire lumen body 22 extending from radiopaque marker band 28 are cut off and the end is polished. The proximal end of guide wire lumen body 22 is then threaded through guide wire entry port 38 using a mandrel to lead the body 22 through the entry port 38. The catheter body is then bonded to the outer band, and the tapered mandrel is inserted into the catheter.

The catheter is then placed on a necking machine and the proximal portion of the outer jacket 18 is drawn down over the fiber bundle 46 and mandrel 30 to create a reduced diameter shaft. The portion of the guide wire lumen body 22 extending beyond guide portion 22 is then trimmed, and the guide wire lumen body 22 is glued to the guide portion 20 using a suitable adhesive such as cyanoacrylate. Proximal marker 26 is cut from a short length of tubing having a color contrasting with that of the outer jacket 18 and is heat fused onto the catheter body at a specified location along its length. The tail tubing 16 is slid over the proximal portion of the outer jacket 18 and the two are heat fused together. The proximal end of the optical fiber bundle 46 is attached to proximal mount 14. Finally, the distal 35 centimeters of the catheter is coated with a hydrophilic BSI coating.

Figure 12:
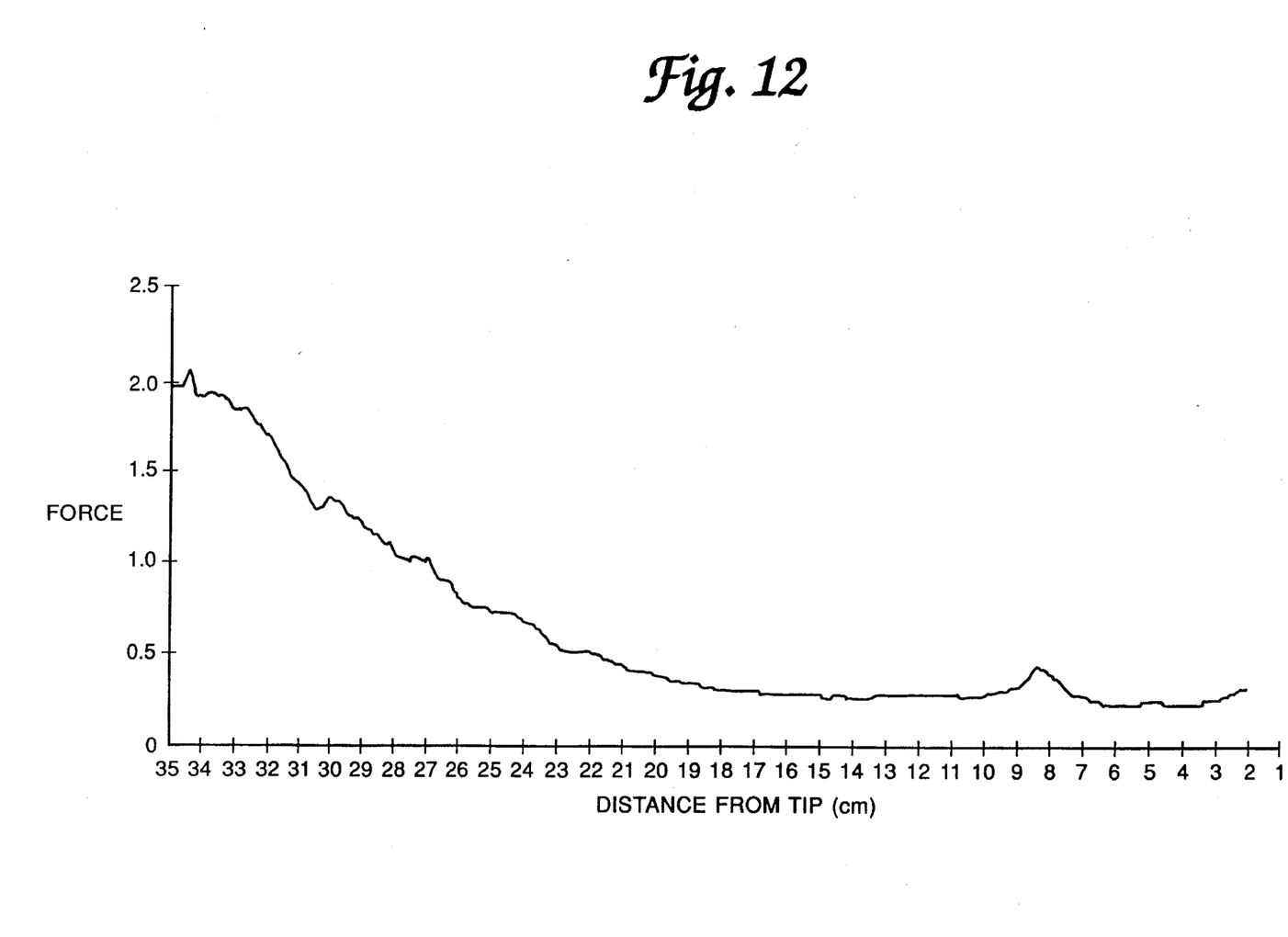
FIGS. 12 and 13 are graphs showing improved trackability characteristics of the present invention.

The combination of the tapered mandrel, optical fibers, low catheter body profile, low durometer guide portion and relatively moveable fibers near the proximal guide wire port cooperate to create a gradually decreasing catheter stiffness profile which enhances catheter tracking and steering. FIG. 12 graphically illustrates the stiffness of the preferred embodiment of the present invention along the length of the catheter. Note that the catheter exhibits a smooth stiffness profile devoid of any abrupt transitions which might tend to degrade trackability and pushability of the catheter. More specifically, this Figure shows the relative amount of force required at a given position to deflect the catheter a given angular amount. As the graph shows, the catheter stiffness tapers off from a relatively high stiffness proximal portion to a distal portion having a constant, relatively low stiffness portion beginning about 20 cm from the distal tip.

Figure 13:
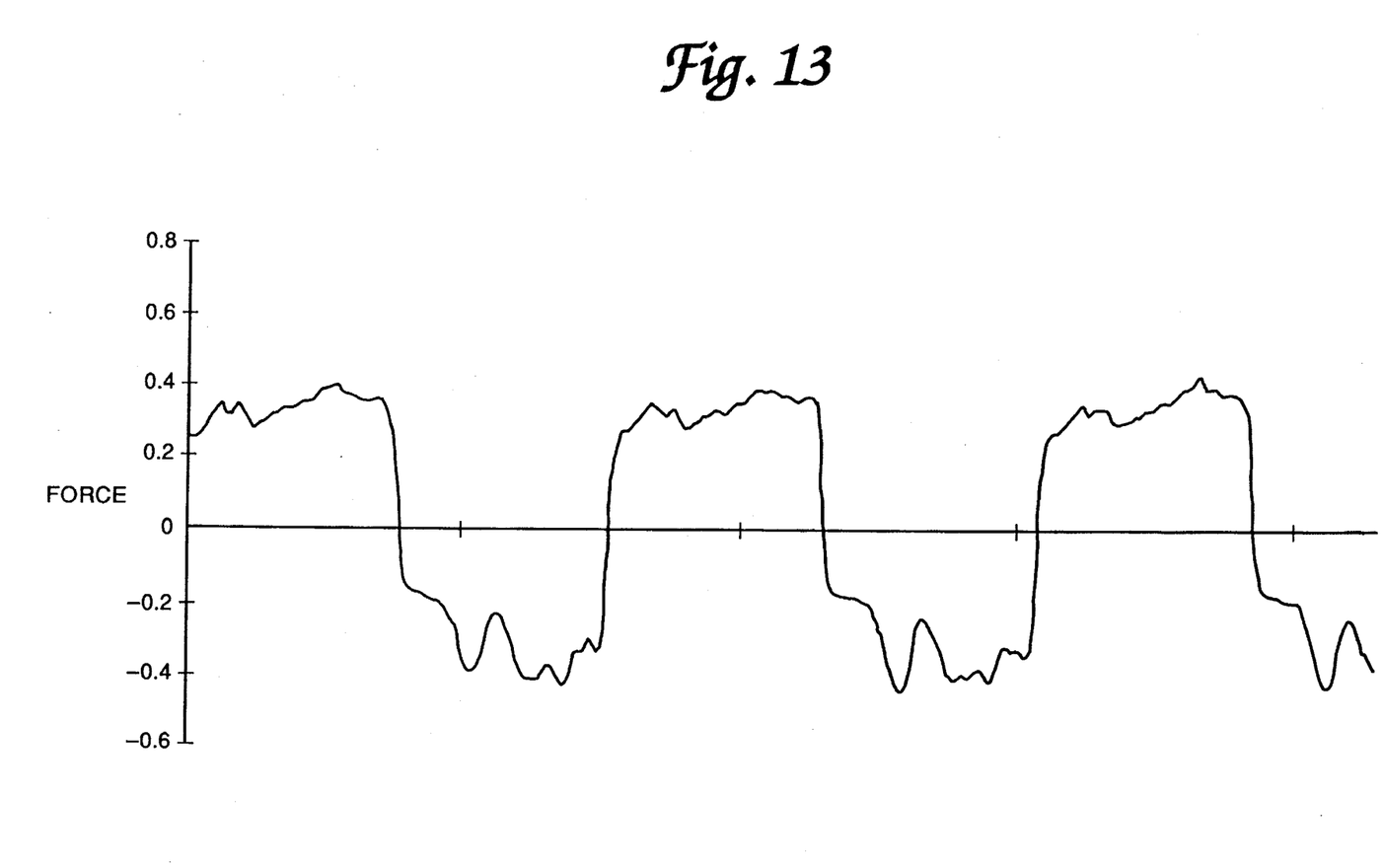

FIG. 13 illustrates the excellent trackability characteristics of a catheter according to the present invention. This Figure shows three passes of the catheter's distal portion in and out of a model heart. The positive portions of this graph represent forward forces necessary to advance the catheter through a coronary passage of the model, and the negative portions of the graph represent backwards forces retracting the catheter from the passage. The vertical portions of the graph represent the end points of catheter travel near the intravascular target area and the catheter's entry point into the coronary ostium, while the roughly horizontal portions represent the tip's transit through the vascular passages. The large bumps on the horizontal represent twists and turns in the tortious passageway. As shown in the graph, only a slight force is required to maneuver the catheter through a vessel, and the catheter's excellent pushability and trackability characteristics help to create a balanced push-pull profile. Note that the catheter requires about the same force to advance it through the model as it does to retract it.

Although a few preferred embodiments of the invention have been shown and described, it will be appreciated by those skilled in the art that changes may be made in these embodiments without departing from the principles and the spirit of the invention, the scope of which is defined in the appended claims.

What is claimed is:

1. A catheter comprising:

a catheter body including a guide portion at a distal end of said catheter body;

a proximal mount disposed on a proximal end of said catheter body;

an optical fiber bundle connected to said proximal mount, said optical fiber bundle extending within said catheter body and said guide portion to a distal end of said guide portion;

a guide wire lumen body extending from said distal end of said guide portion to a proximal portion of said guide portion, an interior surface of said guide wire lumen body defining a guide wire lumen; and wherein a mandrel is disposed within said catheter body and said guide portion and substantially parallel with a longitudinal axis thereof; and wherein said guide wire lumen is less than ten centimeters in length.

2. The catheter of claim 1, wherein said guide wire lumen is about nine centimeters in length.

3. The catheter of claim 1, wherein said mandrel is eccentric to a longitudinal axis of said catheter.

4. The catheter of claim 1, wherein a distal end of said mandrel is coextensive with a proximal portion of said guide wire lumen body.

5. The catheter of claim 1, wherein said catheter body comprises:

a tail tube at a proximal end of said catheter body; and an outer jacket having a proximal end connected to a distal end of said tail tube and a distal end connected to a proximal end of said guide portion;

wherein a proximal end of said mandrel is disposed within a distal end of said tail tube.

6. The catheter of claim 1, further comprising a protective jacket disposed on a distal end of said mandrel.

7. The catheter of claim 1, wherein said mandrel includes a portion tapering to a smaller diameter toward a distal end of said mandrel.

8. The catheter of claim 1, wherein:

a proximal portion of said guide wire lumen body exits said guide portion through an exterior surface of said guide portion to define a guide wire entry port; and a distal portion of said guide wire lumen body terminates substantially coplanar with a distal end of said guide portion to define a guide wire exit port.

9. The catheter of claim 8, wherein said guide wire exit port is eccentric to said longitudinal axis of said catheter.

10. The catheter of claim 1, wherein said proximal portion of said guide wire lumen body does not obstruct said optical fiber bundle.

11. A catheter comprising:

a catheter body including an outer jacket at a proximal portion of said catheter body and a guide portion at a distal end of said catheter body;

an optical fiber bundle extending within said catheter body, a distal end of said optical fiber bundle extending to said distal end of said guide portion;

a guide wire lumen body extending from a proximal end at a proximal portion of said guide portion to a distal end at a distal end of said guide portion, an interior surface of said guide wire lumen body defining a guide wire lumen;

a distal fiber terminator engaging said distal end of said optical fiber bundle and said distal end of said guide wire lumen and maintaining said distal ends of said optical fiber bundle and guide wire lumen in place relative to said distal end of said guide portion; and wherein said guide wire lumen is less than ten centimeters in length;

wherein a mandrel is disposed within said catheter body and said guide portion and substantially parallel with a longitudinal axis thereof;

wherein said guide portion and a portion of said outer jacket collectively define a flexible length of said catheter body at least twenty centimeters in length proximal to said distal fiber terminator, said flexible length being free of any obstructions of said optical fiber bundle.

12. The catheter of claim 11, wherein said guide wire lumen is about nine centimeters in length.

13. The catheter of claim 11, wherein a proximal end of said flexible length is terminated by a proximal mount disposed on a proximal end of said catheter body and connected to a proximal end of said optical fiber bundle.

14. The catheter of claim 11, wherein said mandrel is eccentric to a longitudinal axis of said catheter.

15. The catheter of claim 11, wherein a distal end of said mandrel is coextensive with a proximal portion of said guide wire lumen body.

16. The catheter of claim 11, wherein said catheter body comprises:

a tail tube at a proximal end of said catheter body;

wherein said outer jacket has a proximal end connected to a distal end of said tail tube; and a proximal end of said mandrel is disposed within a distal end of said tail tube.

17. The catheter of claim 11, further comprising a protective jacket disposed on a distal end of said mandrel.

18. The catheter of claim 11, wherein said mandrel includes a portion tapering to a smaller diameter toward a distal end of said mandrel.

19. The catheter of claim 11, wherein:

a proximal portion of said guide wire lumen body exits said guide portion through an exterior surface of said guide portion to define a guide wire entry port; and a distal portion of said guide wire lumen body terminates substantially coplanar with a distal end of said guide portion to define a guide wire exit port.

20. The catheter of claim 19, wherein said guide wire exit port is eccentric to said longitudinal axis of said catheter.

21. A catheter comprising:

a catheter body including a guide portion at a distal end of said catheter body;

a guide wire lumen body less than ten centimeters in length and extending from a proximal portion of said guide portion to a distal end of said guide portion, an interior surface of said guide wire lumen body defining a guide wire lumen;

an optical fiber bundle extending within said catheter body from a proximal portion thereof through said guide portion to a distal end of said guide portion, said optical fiber bundle being moveable relative to said catheter body at said distal end of said catheter body; and varying means disposed within said catheter body at a distal end thereof and substantially parallel to a longitudinal axis thereof, for gradually varying a stiffness profile of said catheter body from a first level at a proximal end of said stiffening means to a second level lower than said first level at a distal end of said stiffening means.

22. The catheter of claim 21, wherein said guide wire lumen is about nine centimeters in length.

23. The catheter of claim 21, wherein said varying means is a mandrel.

24. The catheter of claim 23, wherein said mandrel has a larger cross-sectional area at a proximal end thereof than at a distal end thereof.

25. The catheter of claim 23, wherein said mandrel comprises:

a proximal portion having substantially constant dimensions; and a tapered portion tapering from a distal end of said proximal portion to a distal end of said mandrel.

26. The catheter of claim 23, wherein said mandrel is eccentric to a longitudinal axis of said catheter.

27. The catheter of claim 23, wherein a distal end of said mandrel is coextensive with a proximal portion of said guide wire lumen body.

28. The catheter of claim 23, wherein said catheter body comprises:

a tail tube at a proximal end of said catheter body; and an outer jacket having a proximal end connected to a distal end of said tail tube and a distal end connected to a proximal end of said guide portion;

wherein a proximal end of said mandrel is disposed within a distal end of said tail tube.

29. The catheter of claim 21, wherein:

a proximal portion of said guide wire lumen body exits said guide portion through an exterior surface of said guide portion to define a guide wire entry port; and a distal portion of said guide wire lumen body terminates substantially coplanar with a distal end of said guide portion to define a guide wire exit port.

30. The catheter of claim 29, wherein said guide wire exit port is eccentric to said longitudinal axis of said catheter.

31. A catheter comprising:

a catheter body having a stiffness profile gradually decreasing from a proximal end thereof to a distal end thereof, said distal end of said catheter body including a guide portion having a larger diameter than a remaining portion of said catheter body and being constructed of a material having a lower durometer than a material of which said remaining portion of said catheter body is constructed;

a guide wire lumen body less than ten centimeters in length and extending from a proximal portion of said guide portion intermediate said distal end of said catheter body and a proximal end of said catheter body, to a distal end of said guide portion, an interior surface of said guide wire lumen body being lubricious and defining a guide wire lumen;

varying means disposed within said catheter body at a distal end thereof and substantially parallel to a longitudinal axis thereof, for gradually varying a stiffness profile of said catheter body from a first level at a proximal end of said stiffening means to a second level lower than said first level at a distal end of said stiffening means; and an optical fiber bundle extending within said catheter body from a proximal portion thereof through said guide portion to a distal end of said guide portion, said optical fiber bundle being moveable relative to said catheter body at said distal end of said catheter body.

32. The catheter of claim 31, wherein said varying means comprises:

a proximal portion having substantially constant dimensions; and a tapered portion tapering from a distal end of said proximal portion to a distal end of said mandrel.

33. The catheter of claim 31, further comprising:

a fiber terminator, disposed at a distal end of said guide portion, engaging a distal end of said optical fiber bundle and maintaining said distal ends of said optical fiber bundle and guide wire lumen in place relative to said distal end of said guide portion;

wherein said catheter body includes a flexible portion proximate to said fiber terminator, said flexible portion being free of other fiber obstructions and being at least twenty centimeters in length.

* * * * *